US012760179B2

(12) United States Patent
Mass et al.

(10) Patent No.: US 12,760,179 B2
(45) Date of Patent: Oct. 13, 2026

(54) DYE CROSSLINK

(71) Applicant: Boise State University, Boise, ID (US)

(72) Inventors: Olga A. Mass, Boise, ID (US); William B. Knowlton, Boise, ID (US)

(73) Assignee: Boise State University, Boise, ID (US)

( * ) Notice: Subject to any disclaimer, the term of this patent is extended or adjusted under 35 U.S.C. 154(b) by 1179 days.

(21) Appl. No.: 17/644,620

(22) Filed: Dec. 16, 2021

(65) Prior Publication Data

US 2022/0186035 A1 Jun. 16, 2022

Related U.S. Application Data

(60) Provisional application No. 63/199,262, filed on Dec. 16, 2020.

(51) Int. Cl.
*C09B 67/20* (2006.01)
*G06N 10/20* (2022.01)
*A61K 41/00* (2020.01)

(52) U.S. Cl.
CPC ......... *C09B 67/0063* (2013.01); *G06N 10/20* (2022.01); *A61K 41/0057* (2013.01)

(58) Field of Classification Search
None
See application file for complete search history.

(56) References Cited

U.S. PATENT DOCUMENTS

| | | | | |
|---|---|---|---|---|
| 6,946,675 B2 * | 9/2005 | Braun | B82Y 10/00 | 257/746 |
| 8,207,329 B2 * | 6/2012 | Lindsey | C07D 487/22 | 540/145 |
| 2019/0048036 A1 | 2/2019 | Yurke et al. | | |

OTHER PUBLICATIONS

Chatelain, G., Organic & Biomolecular Chemistry, "Self-assembly of porphyrin-DNA hybrids into large flat nanostructures", 2017, vol. 15, pp. 6257-6263 (Year: 2017).*

Dogutan, D. K., JOC, "Direct Synthesis of Magnesium Porphine via 1-Formyldipyrromethane", 2007, vol. 72, pp. 7701-7714 (Year: 2007).*

Kang, Hyun Suk et al., The Journal of Physical Chemistry, "Effects of Strong Electronic Coupling in Chlorin and Bacteriochorin Dyads", 2016, vol. 120, pp. 379-395 (Year: 2016).*

Bag et al., "Chapter 4—Sonogashira Cross-Coupling: Alkyne-Modified Nucleosides and Their Applications", Palladium-Catalyzed Modification of Nucleosides, Nucleotides and Oligonucleotides, pp. 75-156, 2018.

Biteau et al., "Chapter 3—Suzuki-Miyaura Cross-Coupling as a Synthetic Tool for Nucleoside and Nucleotide Modification", Palladium-Catalyzed Modification of Nucleosides, Nucleotides and Oligonucleotides, pp. 37-74, 2018.

Dalpozzo et al., "Simple and Efficient Chemoselective Mild Deprotection of Acetals and Ketals Using Cerium(III) Triflate", J. Org. Chem., vol. 67, pp. 9093-9095, 2002.

Jiang et al., "Rationally Designed DNA-Origami Nanomaterials for Drug Delivery In Vivo", Advanced Materials, 1804785, pp. 1-6, 2018.

Kim et al., "De Novo Synthesis of Stable Tetrahydroporphyrinic Macrocycles: Bacteriochlorins and a Tetradehydrocorrin", J. Org. Chem., vol. 70, pp. 5475-5486, 2005.

Kobayashi et al., "New Entries to Water-Compatible Lewis Acids", Chem. Eur. J., vol. 12, pp. 5954-5960, 2006.

Krayer et al., "Refined syntheses of hydrodipyrrin precursors to chlorin and bacteriochlorin building blocks", Journal of Porphyrins and Phthalocyanines, vol. 13, pp. 1098-1110, 2009.

Krayer et al., "Expanded Scope of Synthetic Bacteriochlorins via Improved Acid Catalysis Conditions and Diverse Dihydrodipyrrin-Acetals", J. Org. Chem., vol. 75, pp. 1016-1039, 2010.

Pucelik et al., "Bacteriochlorins and their metal complexes as NIR-absorbing photosensitizers: properties, mechanisms, and applications", Coordination Chemistry Reviews, vol. 416, 213340, pp. 1-47, 2020.

Stambasky et al., "C-Nucleosides: Synthetic Strategies and Biological Applications", Chemical Reviews, vol. 109, No. 12, pp. 6729-6764, 2009.

Williams et al., "Mild water-promoted selective deacetalisatison of acyclic acetals", Green Chemistry, vol. 12, pp. 1919-1921, 2010.

Littler et al., "Investigation of Conditions Giving Minimal Scrambling in the Synthesis of trans-Porphyrins from Dipyrromethanes and Aldehydes", J. Org. Chem., vol. 64, pp. 2864-2872, 1999.

* cited by examiner

*Primary Examiner* — Bahar Craigo
(74) *Attorney, Agent, or Firm* — McKee, Voorhees & Sease, PLC

(57) ABSTRACT

DNA has been employed to template dyes into controllable networks of dyes. However, dye-DNA constructs involving covalent tethering often suffer from the lack of structural rigidity due to DNA structural effects (e.g., DNA breathing). Moreover, attachment of a dye to DNA might result in more pronounced structural effects and loss of DNA structural integrity. Employing a dye as a nucleic acid crosslink will reduce deficiencies in DNA structural integrity by creating more rigid, stable, and robust dye-DNA networks while retaining the photophysical benefits of the desired dyes. The utilization of dye crosslinks offers a controllable spacing and orientation of dyes leading to a greater variety in the design of DNA-templated dye networks. Tetrapyrrole type dyes are of a particular interest. A notable chemical diversity of synthetic photo- and chemically stable tetrapyrroles with a variable substitution pattern allows fine-tuning of their chemical and photophysical properties within DNA-templated dye network.

15 Claims, 12 Drawing Sheets

1000

1100

$R_1$, $R_9$:

DYE CROSSLINK

CROSS REFERENCE TO RELATED APPLICATIONS

This application claims priority under 35 U.S.C. § 119 to provisional patent application U.S. Ser. No. 63/199,262, filed Dec. 16, 2020. The provisional patent application is herein incorporated by reference in its entirety, including without limitation, the specification, claims, and abstract, as well as any figures, tables, appendices, or drawings thereof.

STATEMENT REGARDING FEDERALLY SPONSORED RESEARCH OR DEVELOPMENT

This invention was made with government support under Grant Number DE-SC0020089 awarded by the United States Department of Energy. The government has certain rights in the invention.

FIELD OF THE INVENTION

The present invention relates generally to a nucleic acid dye crosslink and/or corresponding method(s) of use and synthesis having applications in at least light-harvesting and energy transfer systems, memory storage, exciton-based devices, optoelectronics, and quantum computing. More particularly, but not exclusively, the present invention relates to a nucleic acid dye crosslink that can be used in network(s) of dyes, high-order DNA nanostructure(s), theragnostics, potent next-generation therapeutic system(s), quantum information systems, and solar harvesting.

BACKGROUND OF THE INVENTION

The background description provided herein gives context for the present disclosure. Work of the presently named inventors, as well as aspects of the description that may not otherwise qualify as prior art at the time of filing, are neither expressly nor impliedly admitted as prior art.

A dye crosslink is a dye molecule covalently attached to two nucleic acid strands. A dye crosslink holds the nucleic acid strands together and prevents their full dissociation. To create a dye crosslink, first, each single nucleic acid strand is tethered with the dye fragment. When two nucleic acid single strands carrying dye fragments approach each other in a solution driven by nucleic acid preorganization forces (e.g., complementary nature of nucleic acids), the fragments being proximate form a full dye molecule.

The chemical reactions to de novo synthesize such tetrapyrroles as chlorins and bacteriochlorins that occur between two "free" tetrapyrrole fragments (i.e., those that are not attached to nucleic acid) are well developed and published. See Kim et al., "De Novo Synthesis of Stable Tetrahydroporphyrinic Macrocycles: Bacteriochlorins and a Tetradehydrocorrin" *The Journal of Organic Chemistry* 2005, 70 (14), 5475-5486; and Krayer et al., "Expanded cope of Synthetic Bacteriochlorins via Improved Acid Catalysis Conditions and Diverse Dihydrodipyrrin-Acetals", *The Journal of Organic Chemistry* 2010, 75 (4), 1016-1039. Likewise, the chemical reactions to synthesize different types of porphyrins from "free" porphyrin fragments are well developed and published. See Littler et. al., "Investigation of Conditions Giving Minimal Scrambling n the Synthesis of Trans-Porphyrins from Dipyromethanes and Aldehydes", *The Journal of Organic Chemistry* 1999, 64 (8), 2864-2872.

General chemistries of small molecule attachment to a single nucleic acid are well developed and published. However, from a synthetic standpoint, the current de novo synthesis of bacteriochlorin allows creation of bacteriochlorins with only a symmetric chemical structure. Moreover, the state of the art has also failed to reveal a nucleic acid crosslink that can simultaneously act as a dye (e.g., a chromophore) and a crosslink.

DNA nanostructures are also known to disassemble under physiological conditions. The application of DNA nanostructures as drug delivery systems is currently considered the most promising application of DNA nanostructures owing to DNA nanostructures high solubility and high cell permeability, yet the state of the art has failed to provide drug delivery systems that prevent such disassembly under physiologically conditions.

Thus, there exists a need in the art for examination and optimization of chemical processes: (i) that include a tetrapyrrole fragment attached to a single nucleic acid strand; and/or (ii) that react at least two tetrapyrrole fragments with one another where each tetrapyrrole fragment has an attached nucleic acid.

SUMMARY OF THE INVENTION

The following objects, features, advantages, aspects, and/or embodiments, are not exhaustive and do not limit the overall disclosure. No single embodiment need provide each and every object, feature, or advantage. Any of the objects, features, advantages, aspects, and/or embodiments disclosed herein can be integrated with one another, either in full or in part.

It is a primary object, feature, and/or advantage of the present invention to improve on or overcome the deficiencies in the art.

It is a further object, feature, and/or advantage of the present invention to allow a dye crosslink to work simultaneously as a covalent crosslink and as a chromophore (dye). This can allow for the creation of a stable and robust dye-nucleic acid network(s) with controllable dye positioning. No additional non-dye crosslinks are needed for said stabilization.

It is still yet a further object, feature, and/or advantage of the present invention to create quantum DNA nanomaterials containing a specific number and alignment of dye crosslinks templated into highly organized dye aggregates. Such quantum DNA nanomaterials can be employed as quantum information systems, optical switches, optoelectronic devices, and light (solar) harvesting systems.

It is still yet a further object, feature, and/or advantage of the present invention to stabilize DNA nanostructure drug delivery systems while delivering this tetrapyrrole to cancer cells.

It is still yet a further object, feature, and/or advantage of the present invention to synthesize both symmetric and asymmetric bacteriochlorins and/or chlorins.

It is still yet a further object, feature, and/or advantage of the present invention to add to the solution a water-compatible catalyst, such as a Lewis acid, to catalyze the reaction between two dye fragments into a full dye molecule. It can be preferred that the reaction to form a dye crosslink between two "free" tetrapyrrole fragments, especially in the case of bacteriochlorin fragments, occurs under mild conditions in the presence of a water compatible catalyst, such as a Lewis acid.

The nucleic acid dye crosslinks disclosed herein can be used in a wide variety of applications. For example, tetrapyrrole (porphyrin, chlorin, bacteriochlorin) crosslink(s) can be incorporated into DNA nanostructures as a next generation therapeutic agent for the photodynamic therapy of cancer and antimicrobial photodynamic therapy (PDT).

Methods can be practiced which facilitate use, manufacture, assembly, maintenance, and repair of dye crosslinks which accomplish some or all of the previously stated objectives.

The dye crosslinks can be incorporated into networks of dyes and complex DNA nanostructures which accomplish some or all of the previously stated objectives.

According to some aspects of the present disclosure, a method of forming a crosslinked dye molecule comprises reacting at least two tetrapyrrole fragments in a solution, driving a solution with direct coupling or through using nucleic acid preorganization forces such that at least two free tetrapyrrole fragments approach one another, and catalyzing the solution using a water compatible catalyst. After driving and catalyzing said solution, a dye molecule is synthesized from proximate fragments selected from at least two free tetrapyrrole fragments. Finally, a covalent linker can tether said dye molecule to (i) two molecular scaffolds or (ii) two sites of one molecular scaffold. The (i) two molecular scaffolds or the (ii) two sites of one molecular scaffold can comprise complementary nucleic acid strands. For example, the complementary nucleic acid strands comprise a single stranded deoxyribonucleic acid ("ssDNA"), a single stranded ribonucleic acid ("ssRNA"), a deoxyribonucleic acid ("DNA"), a single stranded ribonucleic acid ("ssRNA"), a ribonucleic acid ("RNA"), a locked nucleic acid ("LNA"), a peptide nucleic acid ("PNA"), and a bridged nucleic acid "BNA").

According to some additional aspects of the disclosure, the method further comprises hydrolyzing acetals in an aqueous buffer of the solution at a temperature of no more than eighty degrees Celsius (80° C.).

According to some additional aspects of the disclosure, the water compatible catalyst is a Lewis acid selected from the group consisting of: $MgCl_2$, $Sc(OTf)_3$, $Er(OTf)_3$, $Ce(OTf)_3$, $Ga(OTf)_3$, and $Bi(OTf)_3$.

According to some additional aspects of the disclosure, the solution further comprises a metal salt that is an acetate, halide, or triflate selected from the group consisting of: Zn, Pd, Pt, Mg, Ni, Cu, Co, and Cd.

According to some additional aspects of the disclosure, the solution further comprises a base selected from the group consisting of: KOH, NaOH, $Et_3N$, DIEA, and DBU.

According to some additional aspects of the disclosure, the method further comprises coupling dihydrodipyrrins to at least two tetrapyrrole fragments.

According to some additional aspects of the disclosure, the method further comprises modifying the nucleic acid strands with the dihydrodipyrrins and a modifier selected from the group consisting of: an ethynyl oligo modifier, an amino oligo modifier, and an azide oligo modifier.

According to some additional aspects of the disclosure, the method further comprises coupling the dihydrodipyrrins to afford an asymmetric bacteriochlorin product.

According to some additional aspects of the disclosure, the method further comprises cleaving the bacteriochlorin product off the complementary nucleic acid strands with photo- or chemically-cleavable linkers.

According to some additional aspects of the disclosure, the method further comprises recycling the complementary nucleic acid strands and repeating the synthesizing and tethering steps.

According to some additional aspects of the disclosure, the method further comprises allowing for at least two free dihydrodipyrrins to self-couple to bacteriochlorin fragments so that the dye molecule is de novo synthesized.

According to some additional aspects of the disclosure, the method alternatively comprises coupling of two dipyrrins as two tetrapyrrole fragments to afford a porphyrin product.

According to some additional aspects of the disclosure, the method alternatively comprises coupling of a hydrodipyrrin and a dipyrromethene as tetrapyrrole fragments to afford a chlorin product.

According to some additional aspects of the disclosure, the method further comprises controlling spacing, positioning, and angling of the crosslinked dye molecule with respect to at least one another crosslinked dye molecule.

According to some additional aspects of the disclosure, the method further comprises stabilizing a dye-nucleic acid network without the additional non-dye crosslinks.

According to some additional aspects of the disclosure, the method further comprises assembling a DNA nanostructure from the dye crosslink-nucleic acid network.

According to some other aspects of the present disclosure, a dye crosslink comprises at least two pyrrole units forming tetrapyrrole fragments and a nucleic acid strand covalently tethered to each of the tetrapyrrole fragments.

According to some additional aspects of the present disclosure, the pyrrole units comprise a pyrrole ring and a pyrroline ring bridged by a methylene unit.

According to some additional aspects of the present disclosure, the covalent linker is selected from the group consisting of: an alkyl, alkenyl, alkynyl, ester, ether, amide, and amine bond.

According to some other aspects of the present disclosure, a network of dye crosslinks comprises a high order four-stranded DNA nanostructure comprising: non-functionalized nucleotides and at least two tetrapyrrole crosslinks. At least two tetrapyrrole crosslinks comprise interstrand dye crosslinks. The DNA nanostructure is subjected to a coupling reaction in the presence of a water-compatible Lewis acid. The tetrapyrrole crosslinks can further comprise intrastrand dye crosslinks, e.g., the tetrapyrrole crosslinks include a combination of both interstrand dye crosslinks and intrastrand dye crosslinks.

According to some additional aspects of the present disclosure, the tetrapyrrole crosslinks can be (i) each parallelly oriented to one another or (ii) each orthogonally oriented to one another in a junction area.

These and/or other objects, features, advantages, aspects, and/or embodiments will become apparent to those skilled in the art after reviewing the following brief and detailed descriptions of the drawings. Furthermore, the present disclosure encompasses aspects and/or embodiments not expressly disclosed but which can be understood from a reading of the present disclosure, including at least: (a) combinations of disclosed aspects and/or embodiments and/or (b) reasonable modifications not shown or described.

BRIEF DESCRIPTION OF THE DRAWINGS

Several embodiments in which the present invention can be practiced are illustrated and described in detail, wherein like reference characters represent like components throughout the several views. The drawings are presented for exemplary purposes and may not be to scale unless otherwise indicated.

FIG. 1A, in particular, shows a nucleic acid directly coupling two dye fragments with complementary nucleic acid strands (either ssDNA or ssRNA and their complements). In FIG. 1A, the dye forms within a DNA/RNA duplex as an intrastrand crosslink. FIG. 1B, in particular, shows nucleic acid directed coupling of two dye fragments directed by preorganization forces in high-order DNA assemblies like DNA bricks and other DNA nanostructures. In FIG. 1B, a dye forms between two duplexes as an interstrand crosslink.

In FIGS. 3A and 3C, a waved line depicts a covalent linker to a nucleic acid strand. The linker attachment site at the dihydrodipyrrin and bacteriochlorin is not specified.

FIG. 4A, in particular, concerns the dihydrodipyrrin precursor dhdp-2 and demonstrates Suzuki-Miyaura coupling. FIG. 4B, in particular, concerns the dihydrodipyrrin precursor dhdp-1 and demonstrates Heck coupling. FIG. 4C, in particular, concerns the dihydrodipyrrin precursor dhdp-3 and demonstrates Sonagashira coupling. The chemical structure of the covalent linker between a dihydrodipyrrin and a nucleoside is also depicted.

FIG. 5A, in particular, demonstrates use of a Sonagashira reaction between an ethynyl modifier and iodo group of dihydrodipyrrin. FIG. 5B, in particular, demonstrates use of an amidation reaction between an amino modifier and NHS-ester group of dihydrodipyrrin. FIG. 5C, in particular, demonstrates use of a click-reaction between an azide modifier and alkyne group pf dihydrodipyrrin. The resulting covalent linkers are also depicted.

In FIG. 6A, de novo bacteriochlorin synthesis affords a statistical mixture of three bacteriochlorin products due to a side self-coupling of each dihydrodipyrrin. The substitution site(s) $R_1$ and $R_2$ of each dihydrodipyrrin are not specified. In FIG. 6B, nucleic acid directed synthesis affords one asymmetric bacteriochlorin product which can be potentially cleaved off the nucleic acid strands if desired.

FIG. 8A, in particular, shows each fragment contains an electrophilic and nucleophilic reaction center. FIG. 8B, in particular, shows one fragment contains two electrophilic reaction centers, whereas the second chlorin fragment contained two nucleophilic reaction centers. The waved line depicts a covalent linker to a nucleic acid strand; the linker attachment site at the dihydrodipyrrin and bacteriochlorin is not specified.

An artisan of ordinary skill in the art need not view, within isolated figure(s), the high number of distinct permutations of features described in the following detailed description to facilitate an understanding of the present invention.

DETAILED DESCRIPTION OF THE INVENTION

The present disclosure is not to be limited to that described herein. Mechanical, electrical, chemical, procedural, and/or other changes can be made without departing from the spirit and scope of the present invention. No features shown or described are essential to permit basic operation of the present invention unless otherwise indicated.

Figure 1A:
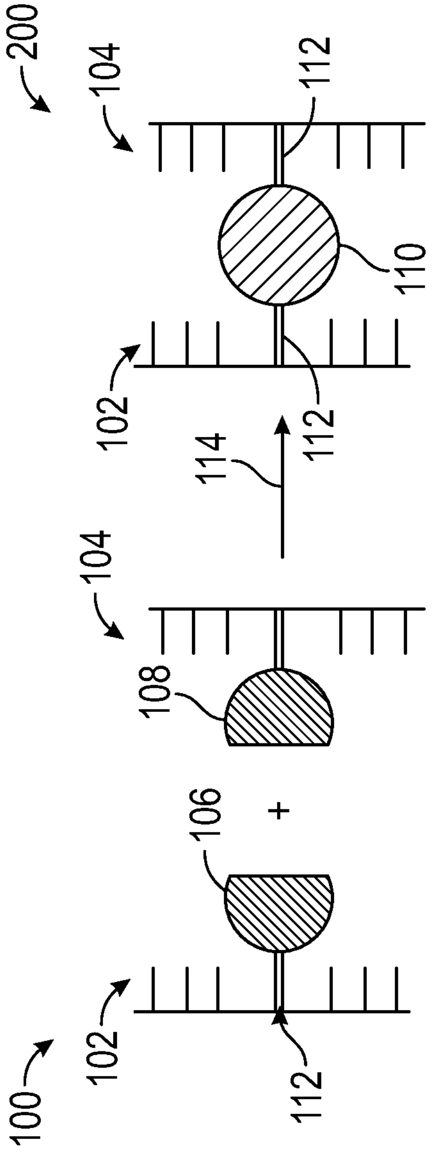
FIGS. 1A-1B show the formation of a dye nucleic acid crosslink.
Figure 1B:
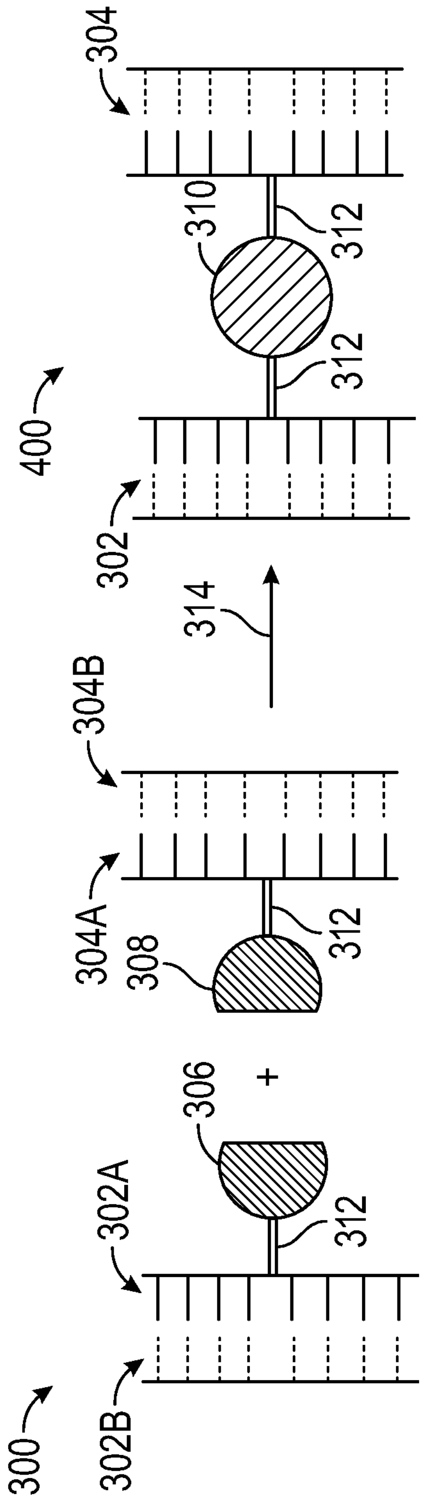

FIG. 1A and FIG. 1B show dye crosslinks 200, 400. The dye crosslinks 200, 400 are dye molecules covalently attached to at least two nucleic acid strands 102, 104, 302, 306. Nucleic acids can include, but are not limited to single stranded deoxyribonucleic acid ("ssDNA"), a deoxyribonucleic acid (DNA), a single stranded ribonucleic acid (ssRNA), a ribonucleic acid (RNA), a locked nucleic acid (LNA), a peptide nucleic acid (PNA), and a bridged nucleic acid BNA).

The dye crosslinks 200, 400 hold the nucleic acid strands together and prevent their full dissociation. In order to create a dye crosslink processes 100, 300, can be carried out. In said processes 100, 300, single nucleic acid strands 102, 104 and/or first components 302A, 304A of DNA/RNA duplexes 302, 304 are tethered to dye fragments 106, 108, 306, 308. When two single nucleic acid strands 102, 104, 302, 304 carrying the dye fragments 106, 108, 306, 308 approach each other in a solution driven by the nucleic acid preorganization forces (e.g., a complementary nature of nucleic acids), the dye fragments couple (i.e., covalently bond) into a full dye molecule 110. The dye fragments 106, 108, 306, 308 can be structurally identical or different. Water- and nucleic acid compatible reagent(s) 114, 314 are added to the solution to catalyze the coupling reaction between two dye fragments 106, 108, 306, 308. The dye crosslink 200, 400 simultaneously serves as a crosslink and as a dye (chromophore).

In FIG. 1A, nucleic acid 102, 104 directed coupling of two dye fragments 106, 108 directed by complementary nucleic acid strands (either ssDNA or ssRNA and their complements) will form a dye 100 within a DNA/RNA duplex as an intrastrand crosslink 200.

In FIG. 1B, nucleic acid 302, 304 directed coupling of two dye fragments 306, 308 directed by preorganization forces in high-order DNA assemblies like DNA bricks and other DNA nanostructures. A dye 310 forms between two duplexes as an interstrand crosslink 400.

Figure 2A:
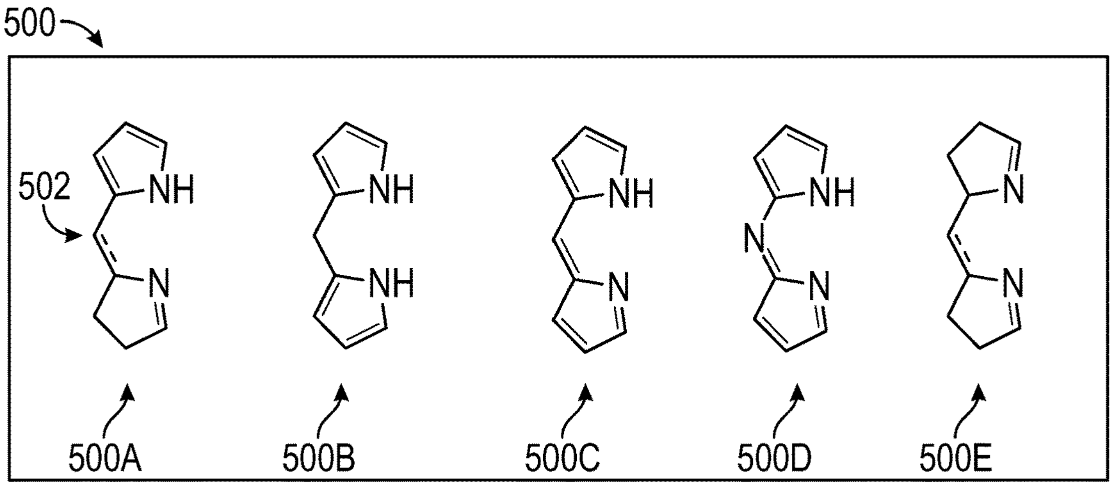
FIG. 2A shows examples of tetrapyrrole fragments (dipyrroles).
Figure 2B:
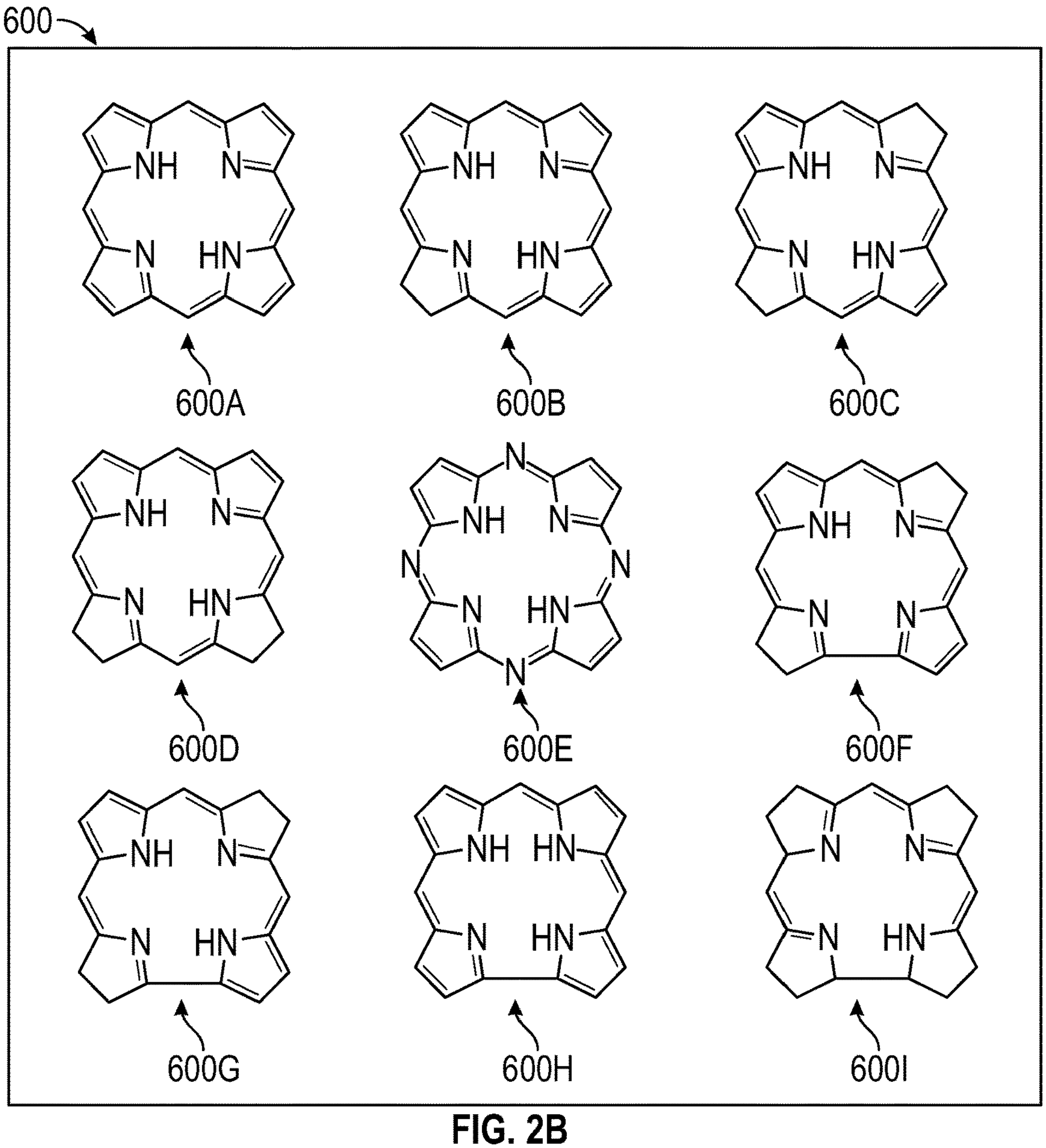
FIG. 2B shows examples of tetrapyrrole-type dyes. The side substituents, covalent linkers, and nucleic acids are omitted in FIGS. 2A-2B.

A tetrapyrrole is a dye composed of four pyrrole (or pyrrole-type) units. A pyrrole is a heterocyclic aromatic organic compound, a five-membered ring with the formula $C_4H_4NH$. Pyrroles are a colorless volatile liquid that darkens readily upon exposure to air. A tetrapyrrole fragment tethered to a nucleic acid can consist of one, two, or three pyrrole units selected with the following chemical structures:

Examples of tetrapyrrole fragments of two pyrrole units, i.e., dipyrroles 500, are shown in FIG. 2A. The dipyrroles 500 shown include hydrodipyrrin 500A, dipyrromethene 500B, dipyrrin 500C, aza dipyrrin 500D, and the chemical structure identified by element 500E. The bond 502 can be a single or double bond.

Depending on the chemical structure of dipyrroles 500, different types of tetrapyrrole macrocycles 600 (e.g., porphyrin 600A, chlorin 600B, bacteriochlorin 600C, isobacteriochlorin 600D, phthalocyanine 600E, tetradehydrocorrin 600F, tetradehydrocorrin 600G, corrole 600H, corrin 600I, etc.) can be created as a nucleic acid crosslink.

The tetrapyrroles 600 (porphyrin, chlorin, bacteriochlorin) crosslink(s) as described herein can be incorporated into DNA nanostructures as a next generation therapeutic agent for the photodynamic therapy of cancer and antimicrobial photodynamic therapy (PDT). While several tetrapyrroles have even been FDA-approved for use in PDT (e.g., Tookad or Visudyne by Novartis), the limitation of their application in photomedicine is restricted by their solubility in water and limited cell permeability. However, using a tetrapyrrole crosslink as described herein can stabilize the DNA nanostructure drug delivery system while delivering this tetrapyrrole to the cancer cells as photosensitizing agent. This can be used for purposes of theragnostics, to synergistically create a potent next-generation therapeutic system, to process quantum information, and/or for harvesting light (including solar power).

Figure 3A:
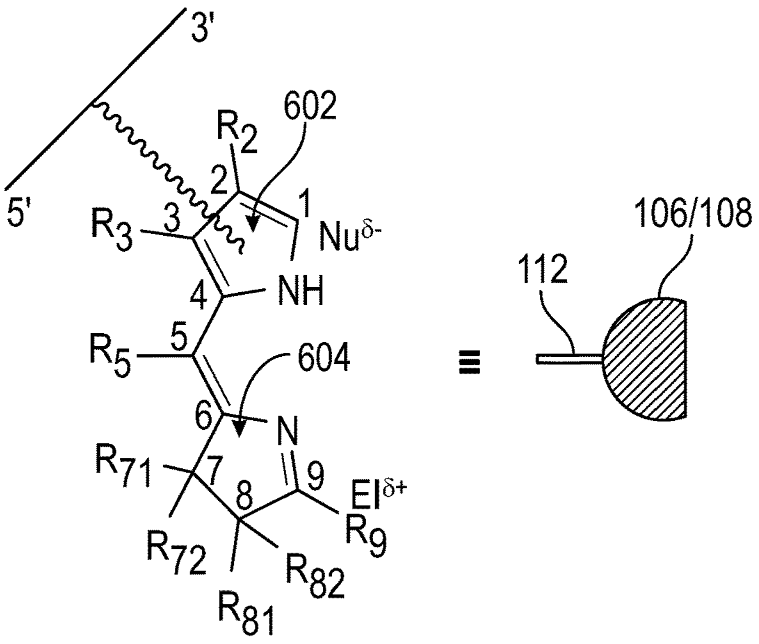
FIG. 3A shows a chemical structure of dihydrodipyrrin as a bacteriochlorin fragment, with the carbon positions of the dihydrodipyrrin numbered 1 through 9 (e.g., Cl is 1, C2 is 2, etc.).

Bacteriochlorin 600C is a tetrapyrrole-type dye consisting of two pyrrole and two pyrroline (reduced pyrrole) units. Dihydrodipyrrin is a bacteriochlorin fragment consisting of a pyrrole ring 602 and a pyrroline ring 604 bridged by a methylene unit, as shown in FIG. 3A. The positions C2, C3, C5, C7, and C8 can carry different substituents $R_2$, $R_3$, $R_5$, $R_7$, and $R_8$ or remain unsubstituted, i.e. $R_{2,3,5,7,8}$=H. However, it is recommended to have either the position C7 or C8 (or both) to be a tertiary $sp^3$ carbon ($R_{71}$, $R_{72}$≠H or/and $R_{81}$, $R_{82}$≠H) in order to prevent adventitious dehydrogenation of the dihydrodyiyrrin and the corresponding bacteriochlorin product. The Cl and α-C are the reactive centers. Specifically, the unsubstituted C1 carbon acts as a nucleophile, whereas electron deficient α-carbon within the R9 substituent acts as an electrophile in the coupling reaction between two dihydrodipyrrins.

Bacteriochlorin 600C is a superb dye employed by purple photosynthetic bacteria in the environments of low light intensity to harvest sun light and transfer its excitation energy to the reaction center to drive the conversion of energy into chemical energy. Bactreiochlorins 600C are the pigments of the photosynthetic antenna LH2, whose organization and function in light-harvesting and energy transfer has fascinated many scientists. Owing to a rigid tetrapyrrole macrocycle with a 16-π electron conjugation system, bacteriochlorins 600C strongly absorb and emit in the red and infrared regions of spectrum, possess very narrow spectral bands with a minimal vibronic component, and exhibit a small Stokes shift. These photophysical characteristics make bacteriochlorins 600C to be desirable dyes for a variety of applications ranging from fundamental sciences and biomedicine to materials sciences.

Bacteriochlorins 600C have been utilized in bioimaging as NIR-chromophores. Because the photons of near-infrared (NIR) light exhibit the maximum depth of tissue penetration, NIR-chromophores are the dyes of choice for in-cell and in vivo imaging.

Figure 3B:
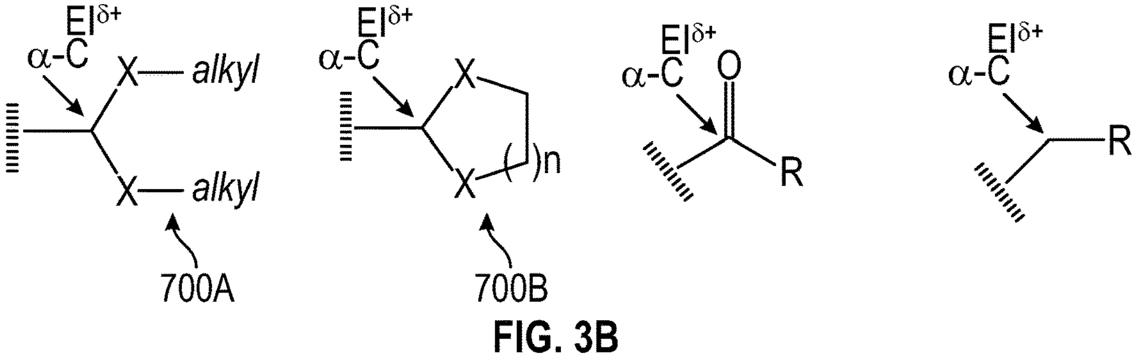
FIG. 3B includes details of acyclic and cyclic acetals.

As shown in FIG. 3B, the examples of $R_9$ substituents include acyclic acetal 700A and cyclic acetal 700B, —C(O)R (R═H, alkyl, aryl, OH, OR', $NR'_2$), and $CH_2R$ (R═OH, OR, $NR_2$, CN, OC(O)R'). The cyclic and acyclic acetals 700B, 700*a* are particularly suited for DNA-compatible coupling, as these chemical groups are known to be activated in aqueous solvent under mild conditions. These mild conditions can include, but are not limited to those conditions described in Table 2 of Williams et al., "Mild Water-Promoted Selective Deacetalisatison of Acyclic Acetals." Green Chemistry 2010, 12 (11), 1919-1921, which is herein incorporated by reference. For example, hydrolysis of acetals can occur in neat water at temperatures of no more than ninety degrees Celsius (90° C.), more preferably no more than eighty degrees Celsius (80° C.), most preferably no more than sixty-five degrees Celsius (65° C.) and/or under no more than eight (8) bar nitrogen pressure afforded.

Figure 3C:
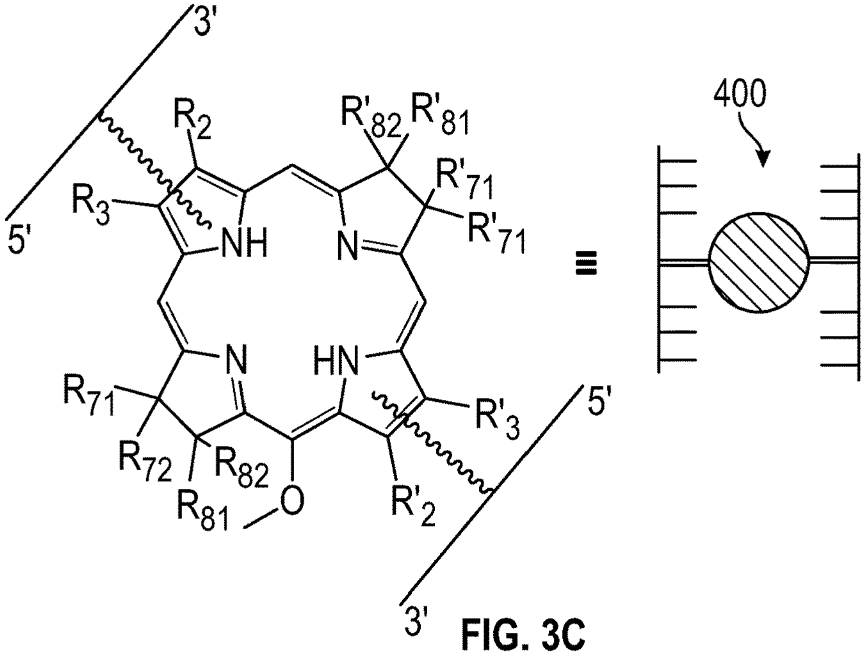
FIG. 3C shows a chemical structure of bacteriochlorin.

As shown in FIG. 3C, each dihydrodipyrrin is covalently linked to a single nucleic acid strand (e.g., ssDNA or ssRNA 102, 104, 302, 304) at 5' end, 3' end, or internally. The covalent linker 112, 312 can include, but is not limited to including, alkyl, alkenyl, alkynyl, ester, ether, amide, and amine bonds. The linker 112, 312 can be attached to the position C2, C3, C5, C7, or C8; also two linkers 112, 312 can be attached to the same dihydrodipyrrin. In general, the covalent attachment of a dihydrodipyrrin molecule to a single nucleic acid strand can be achieved by two ways: (1) during the solid phase synthesis of a single nucleic acid strand 102, 104, 302, 304, or (2) via a post-modification of a single nucleic acid strand 102, 104, 302, 304. The attachment of dihydrodipyrrin to ssDNA or ssRNA 102, 104, 302, 304 during a solid-phase synthesis requires a dihydrodipyrrin-nucleoside.

Figure 4A:
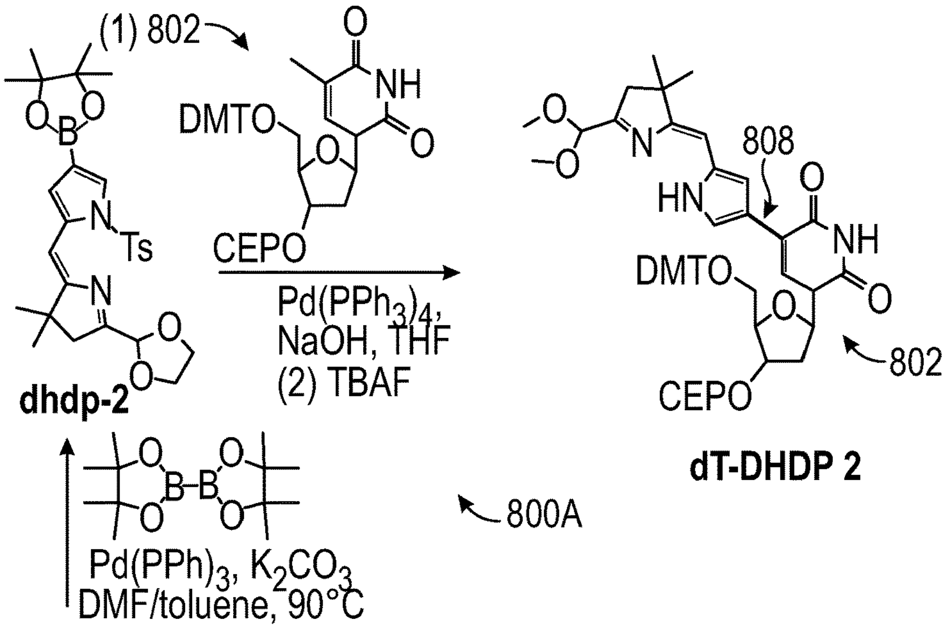
FIGS. 4A-4C demonstrate examples of the synthetic routes to thymine-based dihydrodipyrrin-nucleosides dT-DHDP 2 and dT-DHDP 3 and a non-nucleosidic dihydrodipyrrin-spacer d-DHDP 1 for nucleic acid solid-phase synthesis. The routes start with the common precursor dhdp-1.
Figure 4B:
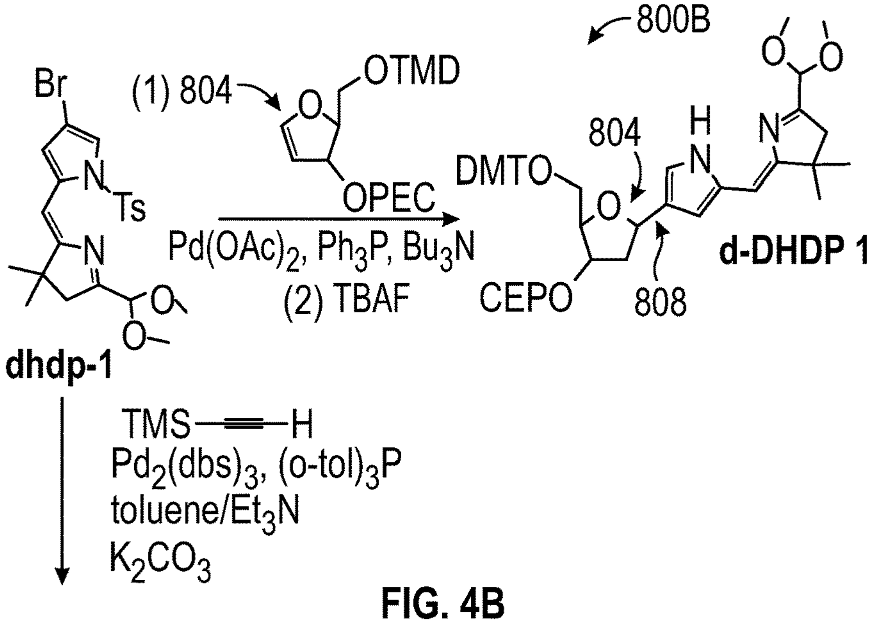
Figure 4C:
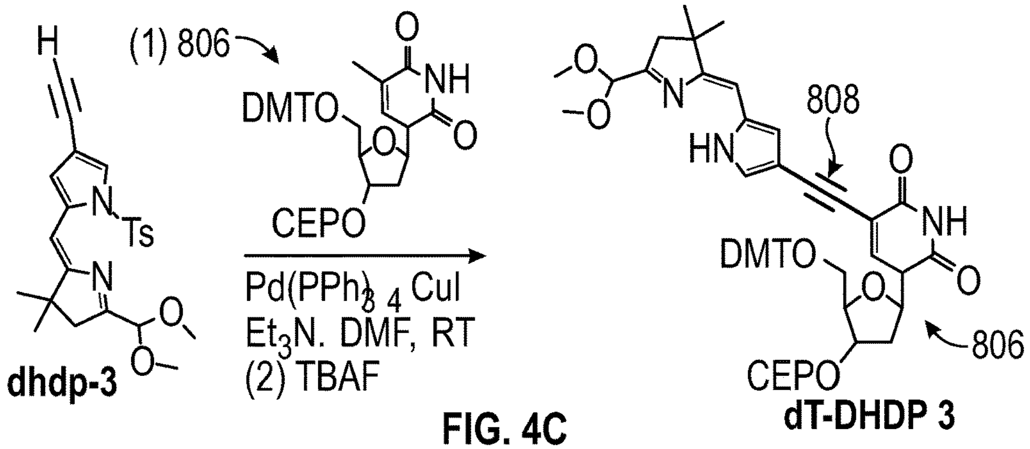

FIGS. 4A-C demonstrate the examples of synthetic routes toward dihydrodipyrrin-nucleosides for the solid-phase synthesis. The synthesis of the dihydrodipyrrin precursor dhdp-1 is well suited for the metal-mediated coupling reactions (e.g., the Suzuki-Miyaura, Heck, and Sonagoshira coupling reactions 800A, 800B, 800C) broadly employed in the nucleoside 802, 804, 806 synthesis.

Examples of the synthetic routes to thymine-based dihydrodipyrrin-nucleosides dT-DHDP 2 and dT-DHDP 3 and a non-nucleosidic dihydrodipyrrin-spacer d-DHDP 1 for nucleic acid solid-phase synthesis are shown in FIGS. 4A-C. The routes start with the common precursor dhdp-1. The chemical structure of the covalent linker 808 between a dihydrodipyrrin (e.g., dhdp-1, dhdp-2, dhdp-3) and a nucleoside 802, 804, 806 for each reaction 800A, 800B, 800C is also depicted.

Figures 5A, 5B, 5C:
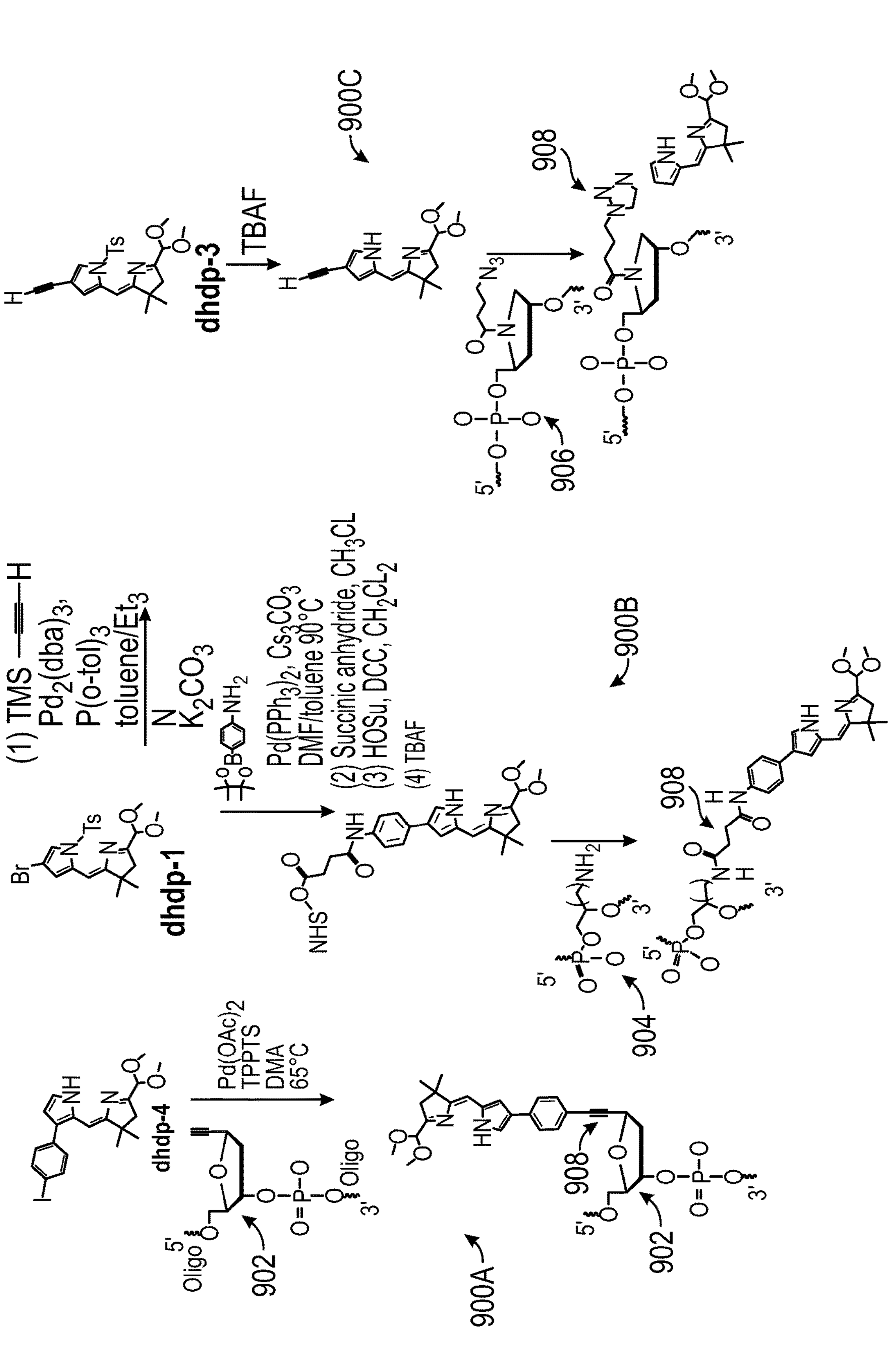
FIGS. 5A-5C demonstrate post-modification strategies of how a dihydrodipyrrin can be covalently attached to a nucleic acid via a reaction between a sequence modifier within the strand and a dihydrodipyrrin.

FIGS. 5A-5C demonstrate distinct post-modification strategies 900A, 900B, 900C of how a dihydrodipyrrin can be covalently attached to a nucleic acid via a reaction between a sequence modifier 902, 904, 906 within the strand and a dihydrodipurrin. The examples of sequence modifiers 902, 904, 906 include amino, azido, alkynyl, and iodo. The sequence modifiers 902, 904, 906 are incorporated into a nucleic acid strand during its solid-phase synthesis.

FIG. 5A shows a Sonagashira reaction between ethynyl modifier 902 and iodo group of dihydrodipyrrin. FIG. 5B shows an amidation reaction between an amino modifier 904 and NHS-ester group of dihydrodipyrrin. FIG. 5C shows a click-reaction between azide modifier 906 and alkyne group pf dihydrodipyrrin. The resulting covalent linker 908 in each of the reactions 900A, 900B, 900C is also shown.

Figure 6A:
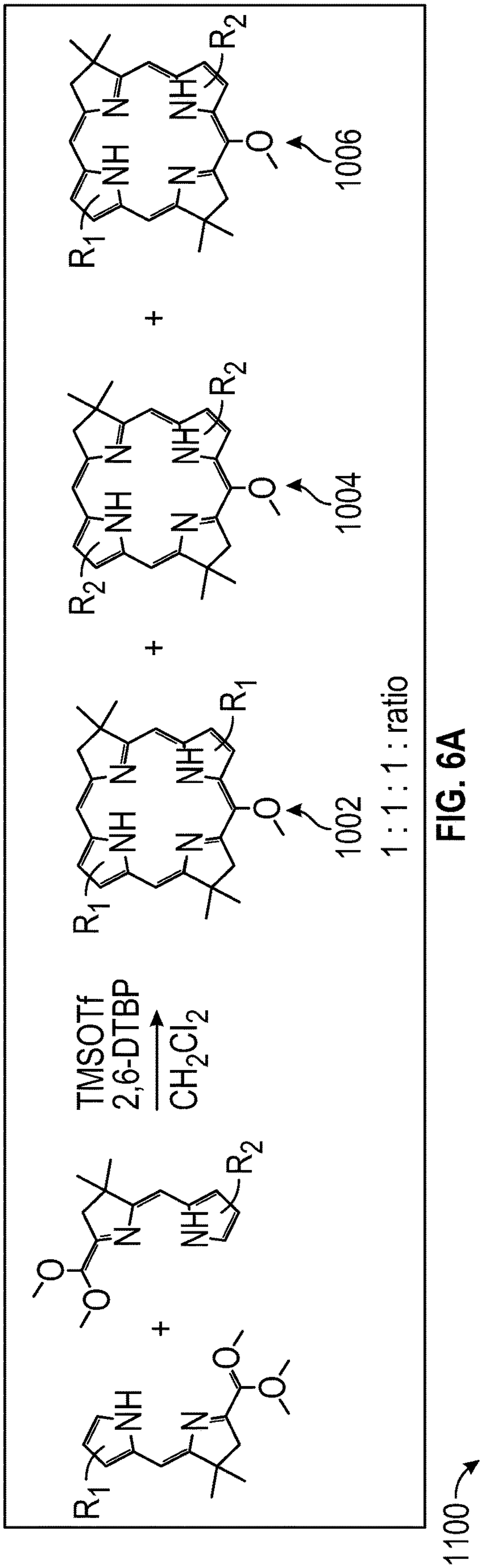
FIGS. 6A-6B compare nucleic acid directed and de novo bacteriochlorin synthesis.
Figure 6B:
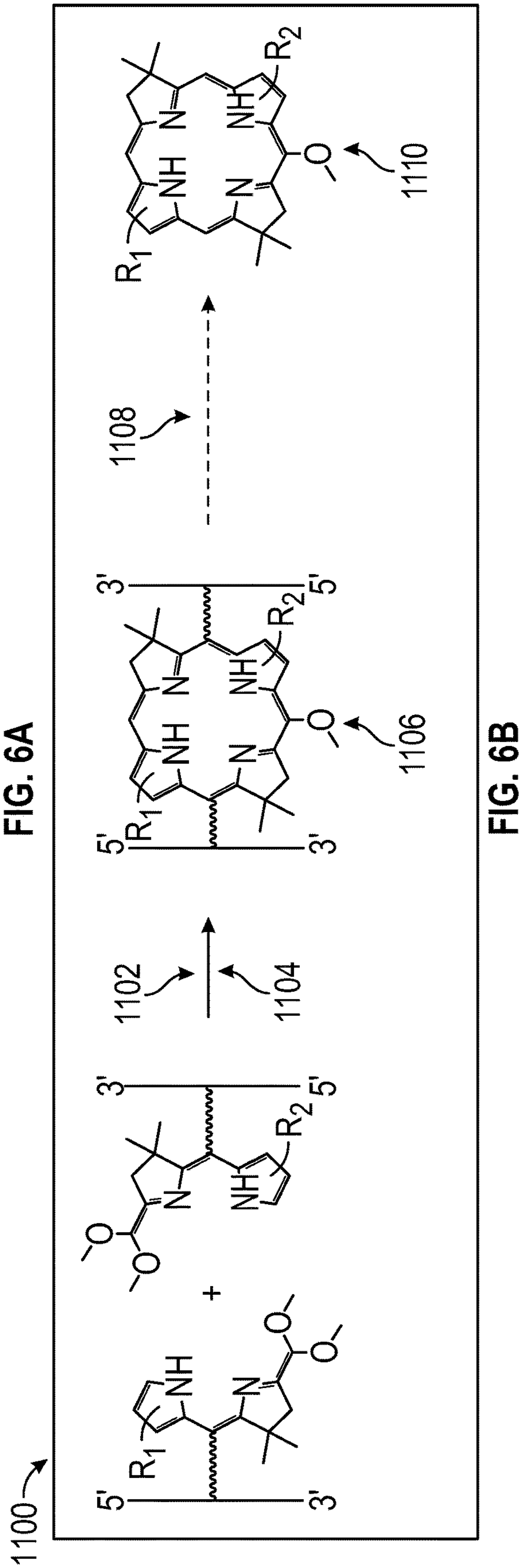

As shown in FIGS. 6A-6B, the coupling reaction involves two distinct or analogical dihydrodipyrrins. Inherent specificity of complementary nucleic acid strand sequences brings two dihydrodipyrrins proximate to each other to allow a directed regioselective coupling reaction into a bacteriochlorin. This method originates from the de novo synthesis of bacteriochlorins where a “free” (i.e., not attached to a nucleic acid strand) dihydrodipyrrin self-couples into a bacteriochlorin. Because of the self-coupling nature, the de novo coupling of two different “free” dihydrodipyrrins affords a statistical mixture of three bacteriochlorins 1002, 1004, 1006 shown in FIG. 6A.

In contrast, when dihydrodipyrrins are attached to complementary nucleic acid strands, the side self-coupling reaction is avoided. Thus, two different dihydrodipyrrins can be coupled to afford an asymmetric bacteriochlorin product 1106, as shown in FIG. 6B. Besides the advantage of the coupling regioselectivity and, in the case of an asymmetric bacteriochlorin, the 3-fold increase in the product yield, the nucleic acid directed coupling is carried out in water rather than in an organic solvent supporting the principles of green chemistry. In addition, if designed with photo- or chemically-cleavable linkers 1108, the bacteriochlorin can be cleaved off the nucleic acid strands to afford a free bacteriochlorin 1110 with the nucleic acid strands recycled to repeat the synthesis.

Figure 7:
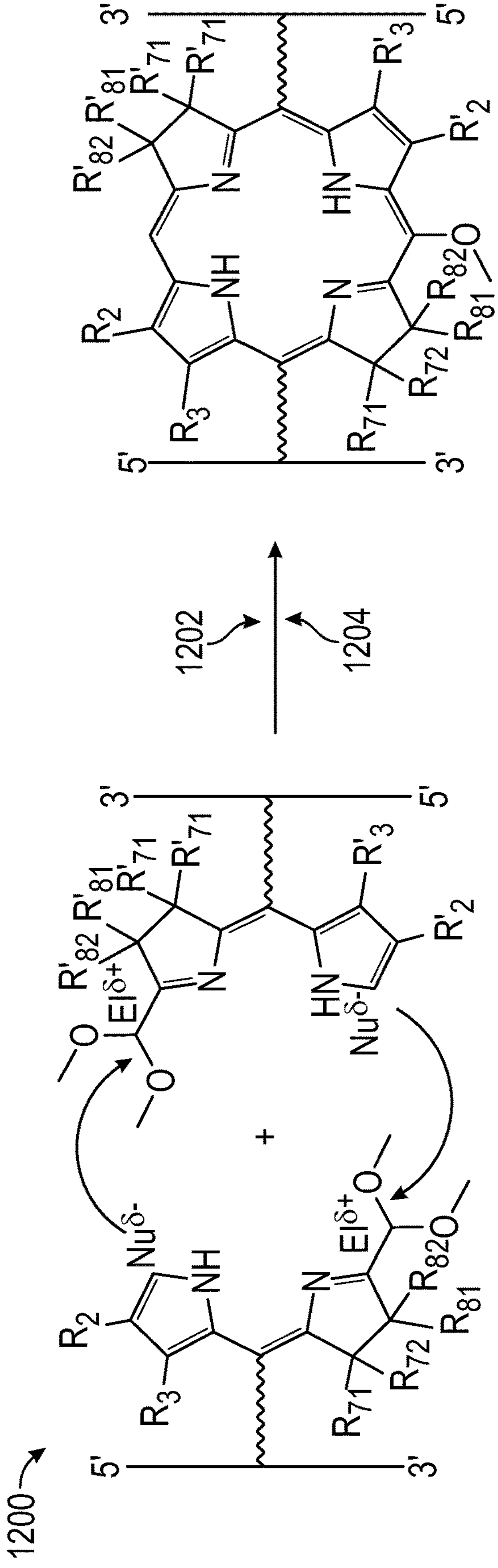
FIG. 7 shows a condensation reaction between two hydrodipyrrins to form a bacteriochlorin. In this example, each hydrodipyrrin is covalently attached to a single nucleic acid strand via the position C5. The $R_9$ group is dimethylacetal. The electrophilic and nucleophilic reaction centers are denoted as $El^{\delta+}$ and $Nu^{\delta-}$ respectively. Two reacting dihydrodipyrrins can carry an identical set of substituents $R_2$, $R_3$, $R_{71}$, $R_{72}$, $R_{81}$, $R_{82}$, and $R_9$ to afford a symmetric bacteriochlorin. Or, two reacting dihydrodipyrrins can carry a distinct set of substituents $R_2$, $R_3$, $R_{71}$, $R_{72}$, $R_{81}$, $R_{82}$, and $R_9$ to afford an asymmetric bacteriochlorin.

Complementary nucleic acid strands with covalently attached dihydrodipyrrins are mixed in water or aqueous buffer 1102/1204/1602/1702 with or without additional salts 1604/1704 (e.g., NaCl, $MgCl_2$, etc.), as shown in FIG. 7. The reaction mixture is annealed or kept at room temperature to allow hybridization. Upon completion of hybridization, a water-compatible Lewis acid 1102/1202/1602/1702 (e.g. $MgCl_2$, $Ga(OTf)_3$, $Bi(OTf)_3$, $Sc(OTf)_3$, $Ce(OTf)_3$) is added to activate the electrophilic α-carbon and catalyze the coupling reaction. The reaction is allowed to proceed from minutes to hours. The temperature is kept at room temperature or elevated to the DNA melting temperature. The reaction progress is monitored spectroscopically at the long wavelength absorption of bacteriochlorin. Due to the high molar extinction coefficient (~$10^5$ $M^{-1}$ $cm^{-1}$) of bacteriochlorin product, a 1% coupling yield can be detected. The product: DNA or RNA duplex crosslinked with a bacteriochlorin that can be purified by dialysis techniques to remove small ions, HPLC, gel electrophoresis, or by a combination of these purification techniques.

Figure 8A:
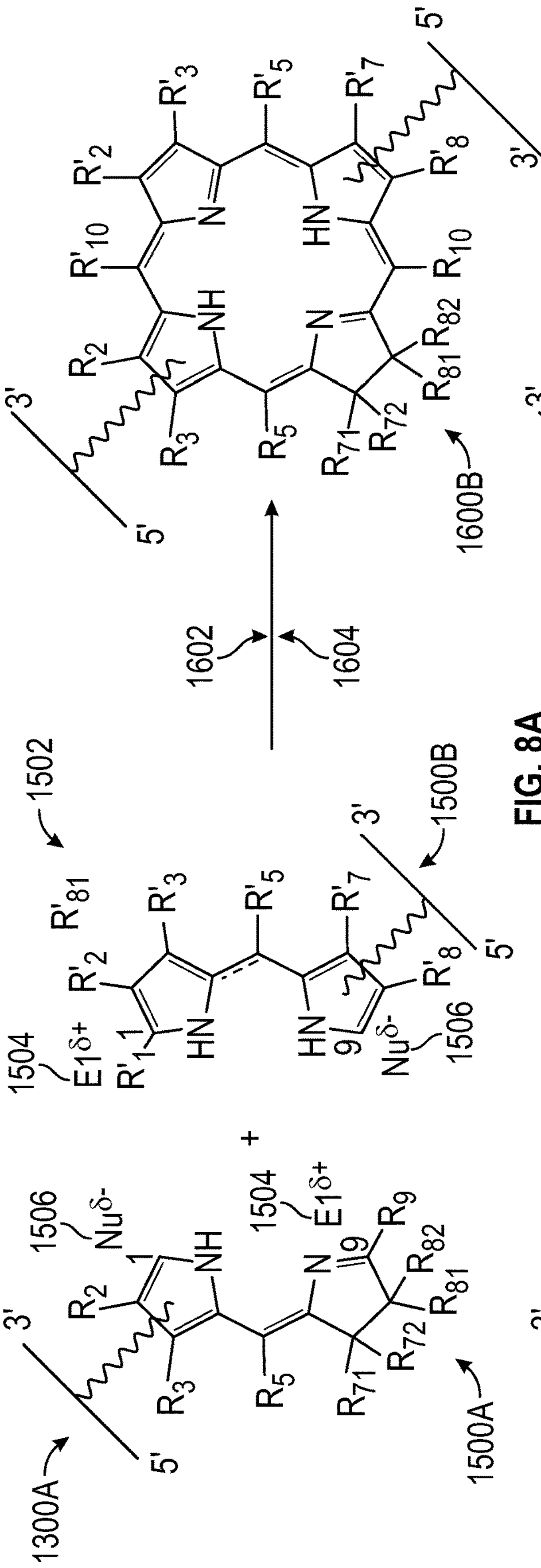
FIGS. 8A-8B show nucleic acid directed coupling of two chlorin fragments.
Figure 8B:
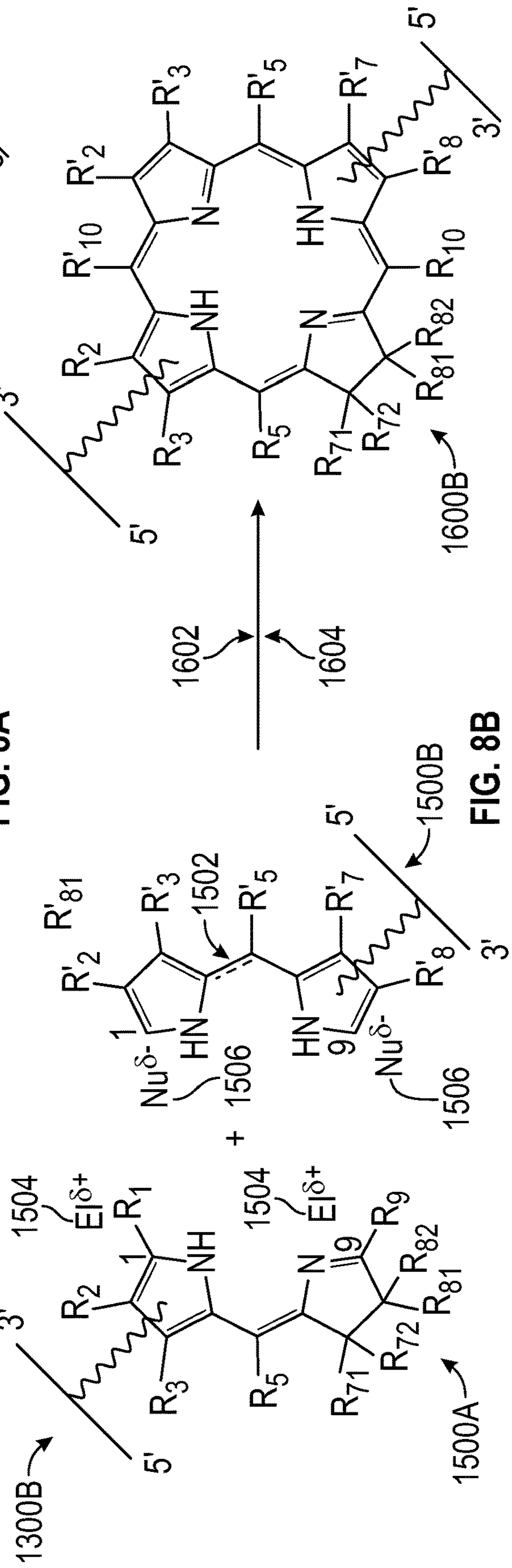

FIGS. 8A-8B show two examples of a nucleic acid directed coupling 1300A, 1300B of two chlorin fragments: hydrodipyrrin 1500A and dipyrromethane 1500B. The fragments 1500A, 1500B combine to form chlorin 1600B. FIG. 8A shows each fragment 1500A, 1500B containing an electrophilic and nucleophilic reaction center. FIG. 8B shows the first fragment 1500A contains two electrophilic reaction centers, whereas the second chlorin fragment 1500B contains two nucleophilic reaction centers. A waved line depicts a covalent linker to a nucleic acid strand; the linker attachment site at the dihydrodipyrrin and bacteriochlorin is not specified.

Examples of Lewis Acids 1602 for the embodiment of FIGS. 8A-8B include $MgCl_2$, $Sc(OTf)_3$, $Er(OTf)_3$, $Ce(OTf)_3$, $Ga(OTf)_3$, $Bi(OTf)_3$, etc. Examples of metal salts 1604 include acetates, halides, and triflates of Zn, Pd, Pt, Mg, Ni, Cu, Co, Cd, etc.

Figure 8C:
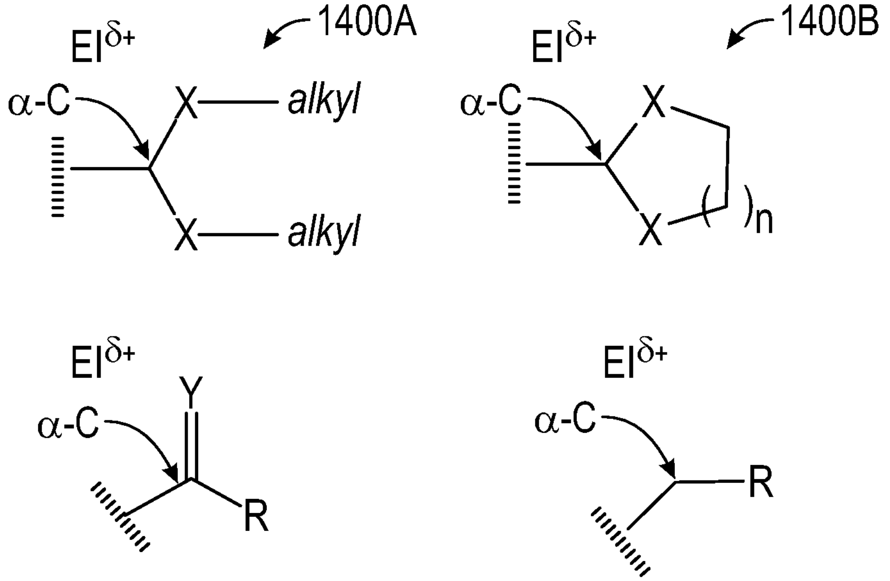
FIG. 8C includes details of acyclic and cyclic acetals.

As shown in FIG. 8C, the examples of $R_1$ and $R_9$ substituents include acyclic acetal 1400A and cyclic acetal 1400B, —C(O)R (R═H, alkyl, aryl, OR', NR'$_2$), and $CH_2R$ (R═OH, OR', CN, $NR_2$, OC(O)R').

Figure 9:
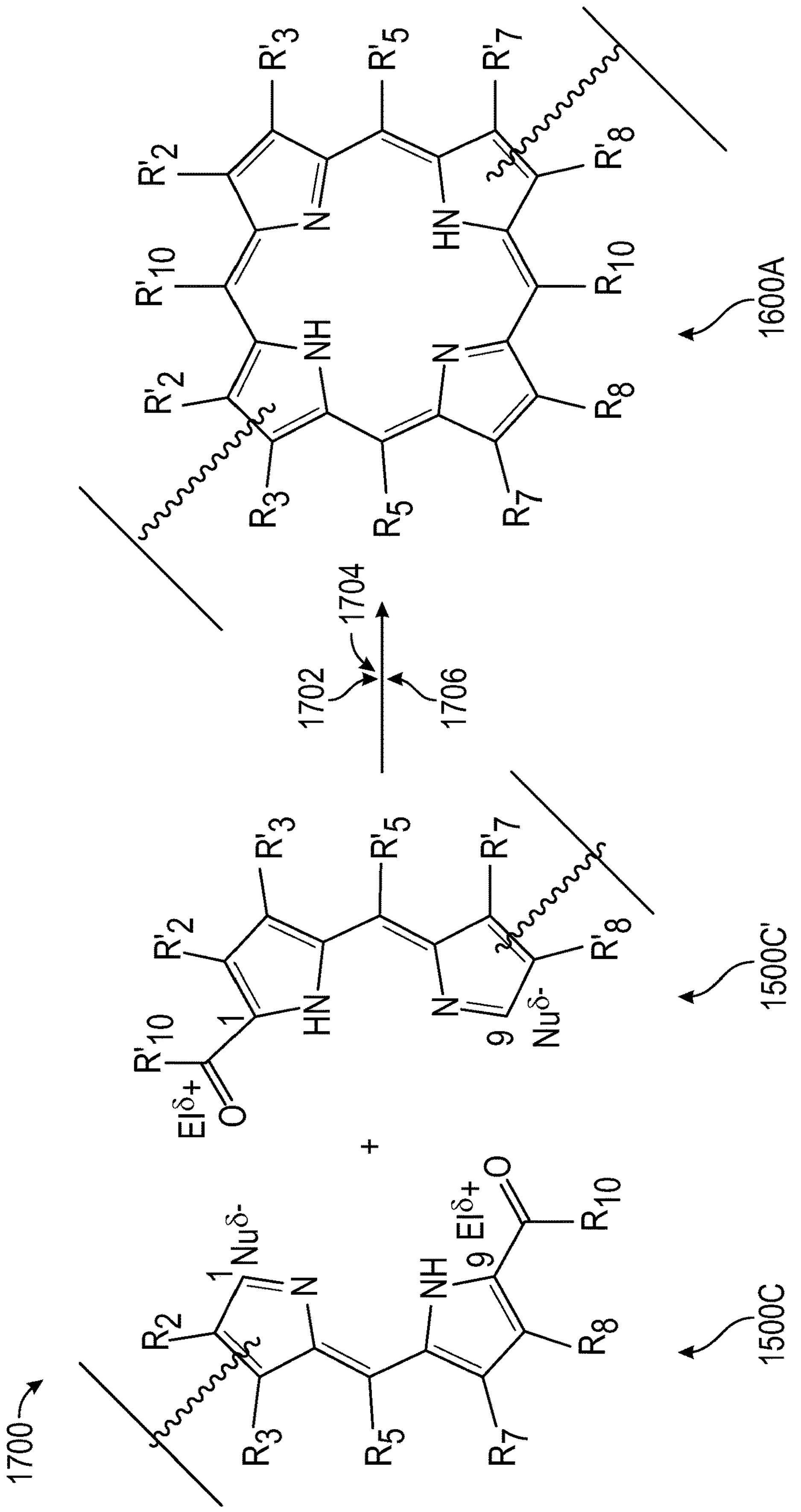
FIG. 9 shows nucleic acid directed coupling of two porphyrin fragments. Each fragment contains an electrophilic and nucleophilic reaction center. A waved line depicts a covalent linker to a nucleic acid strand; the linker attachment site at the dihydrodipyrrin and bacteriochlorin is not specified.

FIG. 9 shows nucleic acid directed coupling 1700 of two porphyrin fragments: dipyrrin 1 and dipyrrin 2 1500C, 1500C'. The fragments 1500C, 1500C' combine to form porphyrin 1600A. Each fragment contains an electrophilic and nucleophilic reaction center. A waved line depicts a covalent linker to a nucleic acid strand; the linker attachment site at the dihydrodipyrrin and bacteriochlorin is not specified.

Examples of Lewis Acids 1702 for the embodiment of FIG. 9 include $MgCL_2$, $Sc(OTf)_3$, $Er(Otf)_3$, $Ce(Otf)_3$, $Ga(Otf)_3$, $Bi(Otf)_3$, etc. Examples of metal salts 1704 include acetates, halides, and triflates of Zn, Pd, Pt, Mg, Ni, Cu, Co, Cd, etc. Example of suitable bases 1706 include KOH, NaOH, $Et_3N$, DIEA, DBU, etc.

Figure 10A:
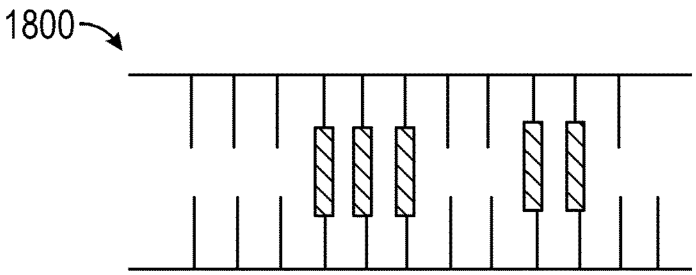
FIG. 10A shows a fragment of a DNA duplex containing five tetrapyrrole crosslinks (squares). The spacing between tetrapyrrole crosslinks is controlled by the number of non-functionalized nucleotides (black lines) between bacteriochlorin molecules.
Figure 10B:
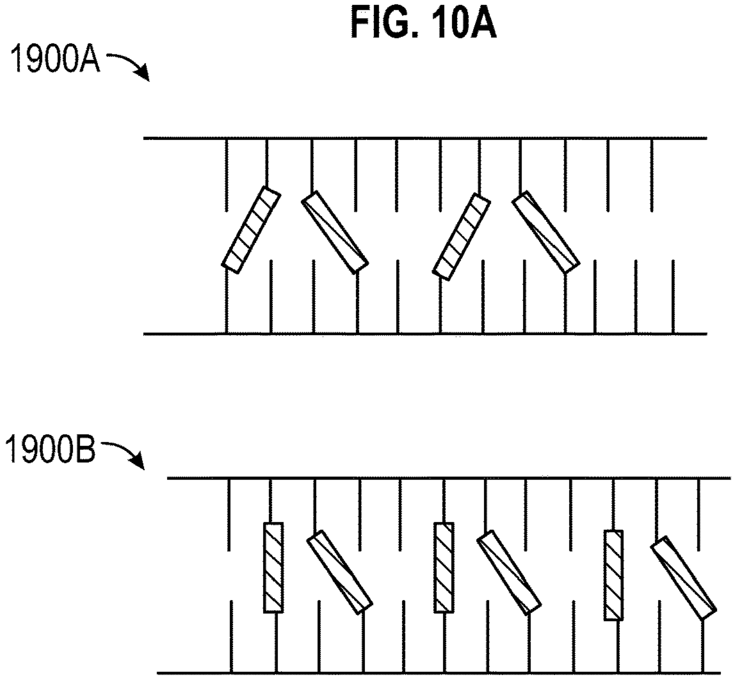
FIG. 10B shows a fragment of DNA containing tetrapyrrole crosslinks with different angles between the tetrapyrrole molecules.

FIGS. 10A-B show a network of dye crosslinks can be created by incorporating a number of dye crosslinks within DNA structure at the specific nucleotide locations. In FIG. 10A, the spacing between dye crosslinks in the network 1800 is controlled by the number of non-functionalized nucleotides (lines) between the dyes. FIG. 10A shows a fragment of DNA duplex containing five tetrapyrrole crosslinks (squares). In FIG. 10B, the angle(s) between dye crosslinks in the networks 1900A, 1900B is controlled by positioning one dye fragment diagonally relative to the second dye fragment to be coupled into a full dye.

Figure 10C:
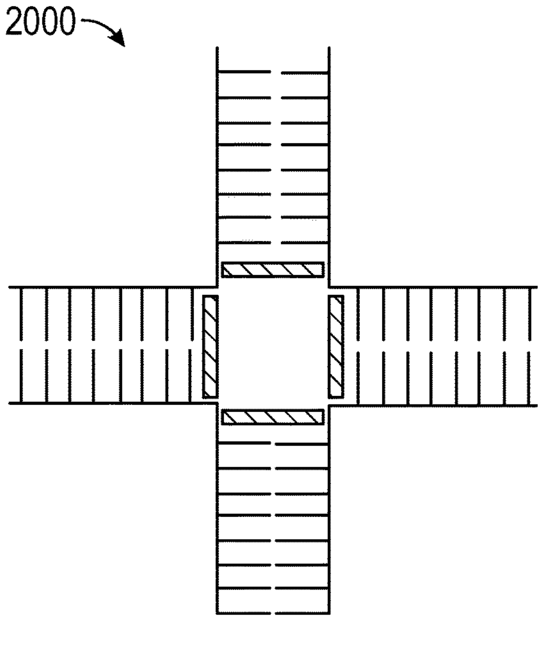
FIG. 10C shows high order 4-stranded DNA (DNA Holliday junction) containing 4 tetrapyrrole crosslinks in the junction area.

FIG. 10C shows a high order 4-stranded DNA (DNA Holliday junction) 2000 containing 4 tetrapyrrole crosslinks in the junction area. In this method variation, dye fragments are covalently attached to complementary or partially complementary nucleic acid single strands self-assembling into high order DNA structures like a three-arm DNA junction and a four-arm DNA junction 2000.

Figure 11:
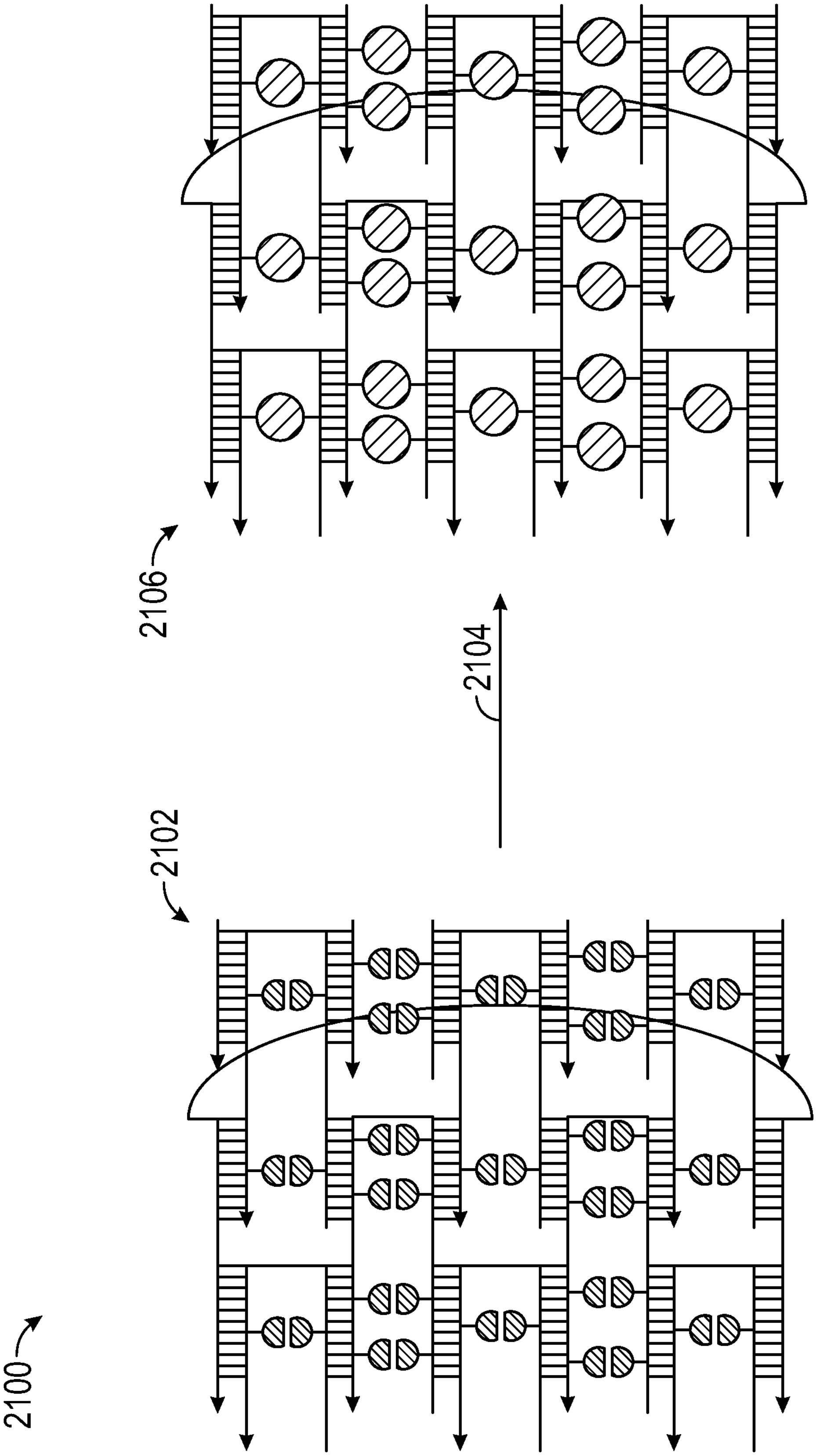
FIG. 11 shows formation of a network of interstrand dye crosslinks in a DNA scaffold (DNA 6-helix tube is used as an example). The regioselective coupling reaction between dye fragments is facilitated by their spatial preorganization within assembled DNA scaffold.

FIG. 11 shows formation of a network 2100 of interstrand dye crosslinks in a DNA scaffold (DNA 6-helix tube is used as an example). The regioselective coupling reaction between dye fragments is facilitated by their spatial preorganization within the assembled DNA scaffold. In this method variation, dye fragments are covalently attached to nucleic acids (complementary or non-complementary) for DNA nanostructure assembly. Preorganization of DNA strands within DNA nanostructure ensures the regioselectivity of the coupling reaction between dye fragments. The proximity of dye fragments is provided by the ordered structure of the DNA nanostructure where the exact position 2102 of each dye fragment is predicted and programmed. In this case, DNA strands can be cross-linked externally (e.g., two DNA duplexes are linked) by an interstrand dye crosslink 400 (FIG. 1B). Once the DNA nanostructure is assembled, the sample is subjected to the coupling reaction in the presence of the catalyst (e.g., water-stable reagents with DNA-compatible conditions 2104 are added) as described above so as to result in a network of dye crosslinks with a stable/robust DNA nanostructure 2106.

According to some other embodiments, both intrastrand and interstrand dye crosslinks 200, 400 are incorporated in a high-order DNA nanostructure.

Again, worth noting is that tetrapyrroles such as porphyrins, chlorins, bacteriochlorin, and phthalocyanines have been found to have a unique ability to selectively accumulate in malignant versus healthy cells resulting in their application as photosensitizers in the photodynamic therapy of cancer (PDT). Several such tetrapyrroles have been FDA-approved for the PDT. Many more tetrapyrroles are currently in Phase I and Phase II medical trials. However, the limitation of their application in photomedicine is restricted by their solubility in water and limited cell permeability. The application of DNA nanostructures as drug delivery systems is currently considered the most promising application of DNA nanostructures owing to DNA nanostructures high solubility and high cell permeability. DNA nanostructures disassemble under physiological conditions. Using tetrapyrrole as a crosslink and a dye in DNA nanostructures and delivering it to the cancer cells as a photosensitizing agent can synergistically create a potent next-generation therapeutic system. Moreover, the use of tetrapyrrole as a crosslink and a dye in DNA nanostructures can also be used for purposes of theragnostics, to process quantum information, and/or for harvesting light (including solar power).

Applicant has described the use of dyes to help process quantum information. For example, in co-owned, co-pending U.S. Ser. No. 17/447,839, titled "BALLISTIC EXCITON TRANSISTOR", filed Dec. 7, 2021, Applicant stated exciton wires may be formed when a series of chromophores are held within the architecture so that when a first chromophore, the "input chromophore," is excited and emits an exciton, the exciton passes, without loss of energy if sufficiently close, to a second chromophore. That chromophore may then pass the exciton to a third chromophore, and so on down a line of chromophores in a wavelike manner. The wires may be straight or branched and may be shaped to go in any direction within the architecture. The architecture may contain one or more wires. Depending on the architecture system used, the exciton wires may be formed along a single nucleotide brick, such as in using the scaffold strand of nucleotide origami, or multiple bricks may comprise the wire, such as in molecular canvases. When two or more wires are brought sufficiently close to each other such that they are nanospaced, the exciton may transfer from one wire to the other. By controlling this transfer, it is possible to build quantum circuits and gates. Some examples of said quantum circuits and gates are described in co-owned, co-pending U.S. patent application Ser. No. 17/447,839, titled ENTANGLEMENT OF EXCITONS BY ACOUSTIC GUIDING, filed Sep. 16, 2021. Quantum algorithms enable the speed-up of computation tasks such as, but not limited to, factoring and sorting. These computations may be performed by an excitonic quantum computer. The excitonic quantum computer can be made from exciton coherence wires, circuits, and gates, such as those described in co-pending, co-owned U.S. Pre-Grant Pub. No. 2019/0048036, titled EXCITONIC QUANTUM COMPUTING MEDIATED BY CHROMOPHORE-EMBEDDED 1-, 2-, AND 3-DIMENSIONAL DNA SCAFFOLDS, published Feb. 14, 2019. Each of the patent disclosures mentioned in this paragraph are herein incorporated by reference in their entireties, including without limitation, the specification, claims, and abstract, as well as any figures, tables, appendices, or drawings thereof.

From the foregoing, it can be seen that the present invention accomplishes at least all of the stated objectives.

LIST OF REFERENCE CHARACTERS

The following table of reference characters and descriptors are not exhaustive, nor limiting, and include reasonable equivalents. If possible, elements identified by a reference character below and/or those elements which are near ubiquitous within the art can replace or supplement any element identified by another reference character.

TABLE 1

| List of Reference Characters | |
|---|---|
| 100 | direct coupling process |
| 102 | first ssDNA/ssRNA |
| 104 | second ssDNA/ssRNA |
| 106 | first dye fragment corresponding with first ssDNA/ssRNA |
| 108 | second dye fragment corresponding with second ssDNA/ssRNA |
| 110 | full dye molecule |
| 112 | covalent linker |
| 114 | nucleic acid directed coupling |
| 200 | intrastrand dye crosslink |
| 202 | component of widget |
| 204 | subcomponent a |
| 206 | subcomponent b |
| 208 | angle between component a and component b |
| 210 | material |
| 212 | characteristic |
| 300 | system directed by preorganization forces |
| 302 | first DNA/RNA duplex |
| 302A | DNA/RNA component |
| 302B | DNA/RNA component |
| 304 | second ssDNA/ssRNA |
| 304A | DNA/RNA component |
| 304B | DNA/RNA component |
| 306 | first dye fragment corresponding with first ssDNA/ssRNA |
| 308 | second dye fragment corresponding with second ssDNA/ssRNA |
| 310 | full dye molecule |
| 312 | covalent linker |
| 314 | nucleic acid directed coupling |
| 306 | first dye fragment corresponding with first ssDNA/ssRNA |
| 400 | interstrand dye crosslink |
| 500 | dipyrroles |
| 500A | hydrodipyrrin |
| 500B | dipyrromethene |
| 500C | dipyrrin |
| 500D | aza dipyrrin |
| 502 | double or single bond |
| 600 | tetrapyrrole macrocycles |
| 600A | porphyrin |
| 600B | chlorin |
| 600C | bacteriochlorin |
| 600D | isobacteriochlorin |
| 600E | phthalocyanine |
| 600F | tetradehydrocorrin |
| 600G | tetradehydrocorrin |
| 600H | corrole |
| 600I | corrin |
| 602 | pyrrole ring |
| 604 | pyrroline ring |
| 700A | acyclic acetal |
| 700B | cyclic acetal |
| 800A | Suzuki-Miyaura coupling |
| 800B | Heck coupling |
| 800C | Sonagashira coupling |
| 802 | nucleoside for Suzuki-Miyaura coupling |
| 804 | nucleoside for Heck coupling |
| 806 | nucleoside for Sonagashira coupling |
| 808 | nucleoside |
| 902 | ethynyl modifier |

TABLE 1-continued

| List of Reference Characters | |
|---|---|
| 904 | amino modifier |
| 906 | azide modifier |
| 908 | covalent linker |
| 1000 | de novo synthesis of "free" bacteriochlorin |
| 1002 | symmetric bacteriochlorin |
| 1004 | symmetric bacteriochlorin |
| 1006 | asymmetric bacteriochlorin |
| 1100 | nucleic acid mediated bacteriochlorin synthesis |
| 1102 | water-compatible Lewis Acid |
| 1104 | aqueous buffer |
| 1106 | asymmetric bacteriochlorin only product |
| 1108 | step for cleaving linkers, recycling nucleic acid strands |
| 1110 | free asymmetric bacteriochlorin |
| 1200 | condensation reaction |
| 1202 | water-compatible Lewis Acid |
| 1204 | aqueous buffer |
| 1300A | nucleic acid directed coupling |
| 1300B | nucleic acid directed coupling |
| 1400A | acyclic acetal |
| 1400B | cyclic acetal |
| 1500A | hydrodipyrrin |
| 1500B | dipyrromethane |
| 1500C | dipyrrin 1 |
| 1500C' | dipyrrin 2 |
| 1600A | porphyrin |
| 1600B | chlorin |
| 1602 | water-compatible Lewis Acid |
| 1604 | metal salt |
| 1700 | nucleic acid directed coupling |
| 1702 | water-compatible Lewis Acid |
| 1704 | metal salt |
| 1706 | base |
| 1800 | network of dye crosslinks |
| 1900A | network of dye crosslinks |
| 1900B | network of dye crosslinks |
| 2000 | DNA Holliday junction |
| 2100 | network of interstrand dye crosslinks |
| 2102 | assembled DNA origami fragment containing external dye fragments at the specific positions |
| 2104 | water-stable reagents with DNA-compatible conditions |
| 2106 | a network of dye crosslinks; stable/robust DNA nanostructure |

Glossary

Unless defined otherwise, all technical and scientific terms used above have the same meaning as commonly understood by one of ordinary skill in the art to which embodiments of the present invention pertain.

The terms "a," "an," and "the" include both singular and plural referents.

The term "or" is synonymous with "and/or" and means any one member or combination of members of a particular list.

The terms "invention" or "present invention" are not intended to refer to any single embodiment of the particular invention but encompass all possible embodiments as described in the specification and the claims.

The term "about" as used herein refer to slight variations in numerical quantities with respect to any quantifiable variable. Inadvertent error can occur, for example, through use of typical measuring techniques or equipment or from differences in the manufacture, source, or purity of components.

The term "substantially" refers to a great or significant extent. "Substantially" can thus refer to a plurality, majority, and/or a supermajority of said quantifiable variable, given proper context.

The term "generally" encompasses both "about" and "substantially."

The term "configured" describes structure capable of performing a task or adopting a particular configuration. The term "configured" can be used interchangeably with other similar phrases, such as constructed, arranged, adapted, manufactured, and the like.

Terms characterizing sequential order, a position, and/or an orientation are not limiting and are only referenced according to the views presented.

A "dye crosslink" is a molecule covalently attached to two molecular scaffolds or two sites of one molecular scaffold. Non-limiting examples of molecular scaffolds include: natural and synthetic oligonucleotides, nucleic acids, peptides, proteins, lipids, carbohydrates, polymers and metal-organic frameworks (MOFs). Dye crosslinks can form by reactive coupling of dye fragments covalently attached to the molecular scaffolds. The coupling reaction can proceed in any solvent (organic or aqueous solvent).

The "scope" of the present invention is defined by the appended claims, along with the full scope of equivalents to which such claims are entitled. The scope of the invention is further qualified as including any possible modification to any of the aspects and/or embodiments disclosed herein which would result in other embodiments, combinations, subcombinations, or the like that would be obvious to those skilled in the art.

What is claimed is:

1. A method of forming a dye molecule, the method comprising:

attaching a first dipyrrole to a first nucleic acid strand;

attaching a second dipyrrole to a second nucleic acid strand;

combining the first and second nucleic acid strands in an aqueous solution, wherein the first and second nucleic acid strands are either (i) complementary strands that hybridize to form a duplex or (ii) non-complementary strands that assemble into a higher order DNA nanostructure; and catalyzing a coupling reaction between the first and second dipyrroles using a water-compatible catalyst to form a dye molecule;

covalently linking the first and second nucleic acid strands, wherein the coupling reaction is regioselective due to the proximity of the first and second dipyrroles provided by the first and second nucleic acid strands.

2. The method of claim 1, wherein:

the first dipyrrole and the second dipyrrole comprises a carbonyl carbon; and the carbonyl carbon comprises an acetal group, and the method further comprises hydrolyzing the acetal into an aldehyde in an aqueous buffer of the solution at a temperature of no more than 80° C.

3. The method of claim 2 wherein the water compatible catalyst is a Lewis acid selected from the group consisting of: $MgCl_2$, $Sc(OTf)_3$, $Er(Otf)_3$, $Ce(Otf)_3$, $Ga(Otf)_3$, and $Bi(Otf)_3$.

4. The method of claim 3 wherein said solution further comprises a metal salt that is an acetate, halide, or triflate of a metal selected from the group consisting of: Zn, Pd, Pt, Mg, Ni, Cu, Co, and Cd.

5. The method of claim 4 wherein said solution further comprises a base selected from the group consisting of: KOH, NaOH, $Et_3N$, DIEA, and DBU.

6. The method of claim 1 wherein the first and second dipyrroles are two identical dihydrodipyrrins, and wherein the method further comprises coupling of the two identical dihydrodipyrrins to afford a symmetric bacteriochlorin product.

7. The method of claim 6 further comprising modifying the complementary nucleic acid strands with the two identical dihydrodipyrrins and a modifier selected from the group consisting of: an ethynyl oligo modifier, an amino oligo modifier, and an azide oligo modifier.

8. The method of claim 1 wherein the complementary nucleic acid strands comprise a single stranded deoxyribonucleic acid (ssDNA) or a single stranded ribonucleic acid (ssRNA) and their complements.

9. The method of claim 1 wherein the complementary nucleic acid strands comprise a locked nucleic acid (LNA), a peptide nucleic acid (PNA), or a bridged nucleic acid (BNA).

10. The method of claim 1 further comprising coupling two non-identical dihydrodipyrrins as the first and second dipyrroles to afford an asymmetric bacteriochlorin product.

11. The method of claim 10, wherein the bacteriochlorin product further comprises a photo- or chemically cleavable linker, wherein the linker links the bacteriochlorin to the nucleic acid strands, and the method further comprises cleaving the bacteriochlorin from the nucleic acid strands to afford a free bacteriochlorin.

12. The method of claim 11 further comprising recycling the complementary nucleic acid strands.

13. The method of claim 1 further comprising processing quantum information using the dye molecule.

14. The method of claim 1 further comprising coupling a hydrodipyrrin and a dipyrromethene as the first and second dipyrroles to afford a chlorin product.

15. The method of claim 1, wherein the first dipyrrole and the second dipyrrole comprises a carbonyl carbon.

* * * * *